United States Patent [19]
Kohr

[11] Patent Number: 6,107,065
[45] Date of Patent: *Aug. 22, 2000

[54] NONSTIRRED BIOREACTOR FOR PROCESSING REFRACTORY SULFIDE CONCENTRATES AND METHOD FOR OPERATING SAME

[75] Inventor: William J. Kohr, San Mateo, Calif.

[73] Assignee: Geobiotics, Inc., Hayward, Calif.

[ * ] Notice: This patent is subject to a terminal disclaimer.

[21] Appl. No.: 08/886,840

[22] Filed: Jul. 1, 1997

Related U.S. Application Data

[63] Continuation of application No. 08/459,621, Jun. 2, 1995, abandoned, which is a continuation-in-part of application No. 08/343,888, Nov. 16, 1994, Pat. No. 5,573,575.

[51] Int. Cl.$^7$ ............... C12P 3/00; C22B 3/18; B01D 53/00

[52] U.S. Cl. ............... 435/168; 75/710; 75/712; 75/743; 423/22; 423/24; 423/27; 423/29; 423/DIG. 17; 435/262; 435/264

[58] Field of Search ............... 435/168, 262, 435/264; 75/710, 712, 743, 744; 423/22, 24, 27, 29, DIG. 17

[56] References Cited

U.S. PATENT DOCUMENTS

| | | |
|---|---|---|
| H1074 | 7/1992 | Lazaroff et al. ............... 204/105 R |
| 588,476 | 8/1897 | Rhodes . |
| 3,777,004 | 12/1973 | Lankenau et al. ............... 423/20 |
| 3,796,308 | 3/1974 | McIlhinney et al. ............... 209/9 |
| 3,819,797 | 6/1974 | Spedden et al. ............... 423/27 |
| 3,949,051 | 4/1976 | Pawlek ............... 423/28 |
| 4,017,309 | 4/1977 | Johnson ............... 75/101 |
| 4,056,261 | 11/1977 | Darrah ............... 266/101 |
| 4,173,519 | 11/1979 | Parker et al. ............... 204/110 |
| 4,256,705 | 3/1981 | Heinen et al. ............... 423/27 |
| 4,256,706 | 3/1981 | Heinen et al. ............... 423/29 |
| 4,269,699 | 5/1981 | McCready et al. ............... 75/101 R |
| 4,279,868 | 7/1981 | Von Kohorn ............... 423/29 |
| 4,301,121 | 11/1981 | Von Kohorn ............... 423/1 |
| 4,318,892 | 3/1982 | Von Kohorn ............... 423/279 |
| 4,324,764 | 4/1982 | Hasegawa et al. ............... 422/159 |
| 4,343,773 | 8/1982 | Miller et al. ............... 423/1 |
| 4,374,097 | 2/1983 | Holland ............... 423/22 |
| 4,402,831 | 9/1983 | Beardsmore et al. ............... 210/606 |
| 4,424,194 | 1/1984 | Hughes ............... 423/1 |
| 4,526,615 | 7/1985 | Johnson ............... 75/101 |
| 4,557,905 | 12/1985 | Sherman et al. ............... 423/27 |
| 4,571,387 | 2/1986 | Bruynesteyn et al. ............... 435/262 |
| 4,585,548 | 4/1986 | Cadzow ............... 209/5 |
| 4,690,894 | 9/1987 | Brierley et al. ............... 435/244 |
| 4,721,526 | 1/1988 | Elmore et al. ............... 75/118 |
| 4,729,788 | 3/1988 | Hutchins et al. ............... 75/118 |
| 4,740,243 | 4/1988 | Krebs-Yuill et al. ............... 75/101 |
| 4,752,332 | 6/1988 | Wu et al. ............... 75/101 |
| 4,778,519 | 10/1988 | Pesic ............... 75/118 |
| 4,789,481 | 12/1988 | Brierley et al. ............... 210/661 |
| 4,888,293 | 12/1989 | Hackl et al. ............... 435/262 |
| 4,987,081 | 1/1991 | Hackl et al. ............... 435/262 |
| 5,006,320 | 4/1991 | Reid et al. ............... 423/150 |
| 5,007,620 | 4/1991 | Emmett, Jr. et al. ............... 266/168 |
| 5,127,942 | 7/1992 | Brierley et al. ............... 75/743 |
| 5,196,052 | 3/1993 | Gross et al. ............... 75/712 |
| 5,232,676 | 8/1993 | Wolff et al. ............... 423/210 |
| 5,236,677 | 8/1993 | Torres-Cardona et al. ............... 423/230 |
| 5,244,493 | 9/1993 | Brierley et al. ............... 75/743 |
| 5,245,486 | 9/1993 | Brierley et al. ............... 75/743 |
| 5,246,486 | 9/1993 | Brierley et al. ............... 423/27 |
| 5,332,559 | 7/1994 | Brierley et al. ............... 423/27 |
| 5,356,457 | 10/1994 | Alvarez et al. ............... 75/710 |
| 5,431,717 | 7/1995 | Kohr ............... 75/744 |
| 5,462,720 | 10/1995 | Aragones ............... 423/27 |
| 5,527,382 | 6/1996 | Alvarez et al. ............... 75/712 |
| 5,573,575 | 11/1996 | Kohr ............... 75/712 |
| 5,611,839 | 3/1997 | Kohr ............... 75/712 |
| 5,763,259 | 6/1998 | Paños ............... 435/262 |
| 5,766,930 | 6/1998 | Kohr ............... 435/262.5 |
| 5,834,294 | 11/1998 | Brierley et al. ............... 435/243 |

FOREIGN PATENT DOCUMENTS

| | | |
|---|---|---|
| 0 522 978 A1 | 10/1992 | European Pat. Off. . |
| 204 900 | 1/1991 | Hungary . |
| 2180829 | 4/1987 | United Kingdom ............ C22B 11/04 |
| WO95/15403 | 6/1995 | WIPO . |

OTHER PUBLICATIONS

Miller et al., Bacterial Heap Leaching of Low–Grade Nickel Material, Council for Mineral Technology, Randburg, South Africa (1985), pp. 341–352.

Southwood et al., Parameters Affecting the Bacterial Heap Leaching of Low–Grade Nicheliferous Material, *Editions GEDIM*, St. Etienne, France (1985), pp. 400–412.

Ahonen, L., et al., Redox Potential–Controlled Bacterial Leaching of Chalcopyrite Ores, Biohydrometallurgical Technologies, The Minerals, Metals & Materials Society (1993) pp. 571–578.

Brierley, C.L., Mineral Bio–Processing: Opportunities in Extractive Metallurgy and Environmental Control, NIST, Nov. 1993, pp. 1–29.

(List continued on next page.)

*Primary Examiner*—Herbert J. Lilling
*Attorney, Agent, or Firm*—Lyon & Lyon LLP

[57] ABSTRACT

A method of biooxidizing sulfide minerals in a nonstirred bioreactor is provided. According to the disclosed method, a concentrate of sulfide minerals is coated onto a plurality of substrates, such as coarse ore particles, lava rock, gravel or rock containing a small amount of mineral carbonate as a source of $CO_2$ for the biooxidizing bacteria. After the sulfide minerals are coated or spread onto the plurality of substrates, a heap is formed with the coated substrates or the coated substrates are placed within a tank. The sulfide minerals on the surface of the plurality of coated substrates are then biooxidized to liberate the metal value of interest. Depending on the particular ore deposit being mined, the sulfide mineral concentrates used in the process may comprise sulfide concentrates from precious metal bearing refractory sulfide ores or they may comprise sulfide concentrates from metal sulfide type ores, such as chalcopyrite, pyrite or sphalorite. The distinction being that in the former, the metal of interest is a precious metal occluded within the sulfide minerals, whereas in the latter, the metal to be recovered is copper, iron, or zinc and is present as a metal sulfide in the sulfide concentrate.

23 Claims, 4 Drawing Sheets

OTHER PUBLICATIONS

Browner, R.E., et al., Studies on the Heap Leaching Characteristics of Western Australian Gold Ores, World Gold (1991).

Fraser, K.S., et al., Processing of Refractory Gold Ores, Minerals Engineering, vol. 4, No. 7–11, pp. 1029–1041, 1991.

Harrington, J.G., et al. Engineering Aspects of Heap Biooxidation of Course–Crushed Refractory Gold Ores, Biohydrometallurgical Technologies, The Minerals, Metals & Materials Society (1993) pp. 521–530.

Henley, K.J., et al., The Mineralogy of Refractory Gold Ores, Biomine '93 Conference, Mar. 22–23, 1993, Adelaide, Australia, pp. 5.1–5.13.

Kelley, B.C., et al., Bioremediation—Applications to Waste Processing in the Mining Industry, Biomine '93 Conference, Mar. 22–23, 1993, Adelaide, Australia, pp. 10.1–10.10.

Merson, J., Mining With Microbes, New Scientist, Jan. 4, 1991, pp. 17–19.

Lizama, H.M., et al., Bacterial Leaching of Copper and Zinc From a Sulfide Ore by a Mixed Culture of Thiobacillus Ferrooxidants and Thiobacillus Thiooxidants in Laboratory Scale and Pilot Plant Scale Columns, Biohydrometallurgy (1989) pp. 519–531.

Mihaylov, B., et al., Biooxidation of a Sulfide Gold Ore in Columns, Mineral Bioprocessing, The Minerals, Metals & Materials Society (1993) pp. 163–177.

Mihaylov, B., et al., Gold Recovery from a Low–Grade Ore Employing biological Pretreatment in Columns, Biohydrometallurgical Technologies, The Minerals, Metals & Materials Society (1993) pp. 499–511.

Nicholson, H., et al., Selection of a Refractory Gold Treatment Process for the Sansu Project, Biomine '93 Conference, Mar. 22–23, 1993, Adelaide, Australia, pp. 20.1–20.11.

Ritchie, A.I.M., et al., Optimisation of Oxidation Rates in Dump Oxidation of Pyrite–Gold Ores, Biomine '93 Conference, Mar. 22–23, 1993, Adelaide, Australia, pp. 9.1–9.8.

Torma, A., Mineral Bioprocessing, Biomine '93 Conference, Mar. 22–23, 1993, Adelaide, Australia, pp. 1.1–1.10.

Untung, S.R., et al., Application of Bio–Leaching to Some Indonesian Sulphide Ores (A Preliminary Study), Biomine '93 Conference, Mar. 22–23, 1993, Adelaide, Australia, pp. 11.1–11.10.

F. Acevedo et al., "Comparative performance of stirred and pachuca tanks in the bioleaching of a copper concentrate", Biohydrometallurgy, pp. 385–394 (Warwick United Kingdom: Science and Technology Letters) (1987).

L. Ahonen and O. H. Tuovinen, "Bacterial Leaching of complex sulfide ore samples in bench–scale column reactors", Hydrometallurgy 37, pp. 1–21 (1995).

G.F. Andrews et al., "Combined physical/microbial beneficiation of coal using the flood/drain bioreactor", Fuel Processing Technology 40, pp. 2–33, 283–296 (1994).

Anonymous, Study Shows Improved Gold Extraction, the Mining Record (1993).

Piero M. Armenante, "Bioreactors, Biotreatment of Industrial and Hazardous Waste," M. A. Levin and M. A. Gealt, Chap. 4, pp. 65–112 (McGraw–Hill, New York) (1993).

Y. A. Attia et al., "Cleaning and desulfurization of high–sulfur coal by selective flocculation and bioleaching in a draft tube fluidized bed reactor", Processing and Utilization of High–Sulfur Coals IV (Elsevier Science Publishers B.V., Amsterdam) (1991).

A. D. Bailey and G. S. Hansford, "Effect of removal of unattached cells on the bio–oxidation rate of pyrite in a fluidised bed reactor", Biotech. Lett., vol. 15, No. 5, pp. 543–548 (1993).

A. D. Bailey and G. S. Hansford, "A fluidised bed reactor as a tool for the investigation of oxygen availability on the biooxidation rate of sulphide minerals at high solids concentrations", Minerals Eng., vol. 6, No. 4, pp. 387–396 (1993).

V. Bakoyianis and A.A. Koutinas, "A Catalytic Multistage Fixed–Bed Tower Bioreactor in an INdustrial–Scale Pilot Plant for Alcohol Production", Biotechnology and Bioengineering, vol. 49, pp. 197–203 (1996).

J. W. Bennett et al., "Limitations on pyrite oxidation rates in dumps set by air transport mechanisms", International Symposium of Biohydrometallurgy, pp. 551–561 (Warwick United Kingdom: Science and Technology Letters) (1987).

M. Beyer, "Microbial removal of pyrite from coal using a percolation bioreactor", Biotech. Letters, vol. 9, No. 1, pp. 19–24 (1987).

M. L. Blasquez et al., "Coal biodesulphurization: A review", Biorecovery, vol. 2, pp. 155–177 (1993).

M. Boon et al., "Mechanisms and Rate Limiting Steps in Bioleaching of Sphalerite, Chalcopyrite and Pyrite with *Thiobacilus ferrooxidans*," Biohydrometallurgical Technologies, pp. 217–235 (Jackson Hole, Wyoming: The Minerals, Metals and Materials Society (1993).

J. A. Brierley et al., "Biooxidation–Heap Concept for Pretreatment of Refractory Gold Ore", Biohydrometallurgical Technologies, pp. 1–30, (Jackson Hole, Wyoming: The Minerals, Metals and Materials Society (1993).

J. A. Brierley, "Bacterial Processes for Transformation of Metals", Environmental Speciation and Monitoring Needs for Trace Metal–Containing Substances from Energy–Related Processes, pp. 264–273 (New Mexico Institute of Mining and Technology) (1981).

Al Bruynesteyn, "Biological Treatment of Refractory Gold Ores—Advantages and Disadvantages", BioMine '93, 3–1 to 3–7 (Adelaide, South Australia, Australian Mineral Foundation) (1993).

Julia R. Budden et al., "Pilot Plant Test Work and Engineering Design for the BacTech Bacterial Oxidation Plant at the Youanmi Mine", BioMine '94, 4.1 to 4.8 (Perth, South Australia, Australian Mineral Foundation) (Sep. 19–20, 1994).

Julia R. Budden, "Bacterial Oxidation Fact and Fallacy", BioMine '93, 19–1 to 19–3 (Adelaide, South Australia, Australian Mineral Foundation) (1993).

A. Burbank et al., "Biooxidation of Refractory Gold Ores in Heaps", Advances in Gold and Silver Processing at GOLDTech 4 (Society of Mining, Metallurgy and Exploration, Inc.) (1990).

Paul D. Chamberlin, "Status of Heap, Dump, and in Situ Leaching of Gold and Silver", World Gold, pp. 225–232 (1989).

Marie–Noelle Collinet et al., "Characterization of arsenopyrite oxidizing *Thiobacillus*. Tolerance of arsenite, arsenate, ferrous and ferric iron", vol. 57, pp. 237–244, (Antonie van Leeuwenhoek) (1990).

M. A. Cornachione et al., "Laboratory Investigation of Bio–Heap Leaching to Remove Sulfer from Kiln Feed Materials", Mining Engineering, pp. 153–156 (Feb. 1994).

M. T. Corral et al., "Continuous Bioleaching of Mineral Sulphide", Biohydrometallurgical Technologies (Jackson Hole, Wyoming: The Minerals, Metals and Materials Society (1993).

K. Czeschka et al., "Influence of biosurfactant producing microorganisms on the hydrocarbon degradation by an original soil population in a percolated soil fixed bed reactor," (Institut für Biochemie und Biotechnolgie, Germany).

Laura L. Damon, "Heap Leach Study of Gilt Edge Sulfide Ore", Black Hills Fifth Western Reg. Conf. on Precious Metals, Coal and the Environment, pp. 47–59 (1994).

H.L. Ehrlich, "Bioleaching of silver from a mixed sulfide ore in a stirred reactor", Biohydrometallurgy, pp. 223–231 (Warwick United Kingdom: Science and Technology Letters) (1987).

G. M. Fraser, "Mixing and Oxygen Transfer in Mineral Bioleaching", pp. 16.1–16.11, (Biomine '93 Conference, Mar. 22–23, 1993, Adelaide, South Africa).

"Slurry Biodegradation", Hazardous Waste Remediation: Innovative Treatment Technologies, Chap. 4, pp. 29–35 (Edited by H.M. Freeman and E.F. Harris. Technomic Publishing Co., Inc. (1995).

"Composting of Contaminated Soil", Hazardous Waste Remediation: Innovative Treatment Technologies, Chap. 8, pp. 73–86 (Edited by H.M. Freeman and E.F. Harris. Technomic Publishing Co., Inc. (1995).

"Heap Pile Bioremediation", Hazardous Waste Remediation: Innovative Treatment Technologies, Chap. 9, pp. 87–100 (Edited by H.M. Freeman and E.F. Harris, Technomic Publishing Co., Inc. (1995).

Chunsheng Fu et al., "Studies on Contaminant Biodegradation in Slurry, Wafer, and Compacted Soil Tube Reactors," Environ. Sci. Technol., vol. 30, No. 3. pp. 743–750 (1996).

Marcel J. Geerdink et al., "Model for microbial degradation of nonpolar organic contaminants in a soil slurry reactor," Environ. Sci. Technol., vol. 30, pp. 779–796. (1996).

Murray R. Gray et al., "Biological remediation of anthracene–contaminated soil in rotating bioreactors." Appl. Microbiol. Biotechnol., vol. 40, pp. 933–940 (1994).

E. A. Griffin et al., "Bioreactor development with respect to process constraints imposed by bio-oxidation and waste remediation," Appl. Biochem. and Biotech, Vols. 24–25, pp. 627–635 (1990).

Ralph P. Hackl, "Operating a commercial–scale bioleach reactor at the Congress gold property," Mining Engineering, vol. 42(12), pp. 1325–1326 (1990).

G. S. Hanford et al., "A propagating–pore model for the batch bioleach kinetics of refractory gold–bearing pyrite", pp. 345–358 (Warwick United Kingdom: Science and Technology Letters) (1987).

J. G. Harrington et al., "Kinetics of Biooxidation of Coarse Refractory Gold Ores", Hydrometallurgy: Fundamentals, Technologies and Innovations (Society of Mining, Metallurgy and Exploration) (Salt Lake City 1993).

M. N. Herrera et al., "A Phenomenological Model of the Bioleaching of Complex Sulfide Ores", Hydrometallurgy, vol. 22, pp. 193–206 (1989).

Warwick Hoffmann et al., "Design of a reactor bioleach process for refractory gold treatment," FEMS Micro. Rev., vol. 11(1–3), pp. 221–230 (1993).

R. W. Lawrence, "Biotreatment of Gold Ores", Microbial Mineral Recovery, pp. 127–148 (H.L. Ehrlich and C.L. Brierly, Editors—1990, McGraw–Hill, New York).

Eric Livesey–Goldblatt, "Bacterial Leaching of Gold, Uranium, Pyrite Bearing Compacted Mine Tailing Slimes", Fundamental and Applied Biohydrometallurgy, Proceedings of the Sixth International Symposium on Biohydrometallurgy, pp. 89–96 (Vancouver, B.C., Canada) (1985).

Andrew G. Livingston, "Biodegradation of 3,4–dichloroaniline in a fluidized bed bioreactor and a steady–state biofilm kinetic model," Biotech. and Bioeng., vol. 38, pp. 260–272 (1991).

G. Loi et al., "Bioreactor performance versus solids concentration in coal biodepyritization," Fuel Processing Technology, vol. 40, pp. 251–260 (1994).

Jock McGregor and Gene E. McClelland, "Agglomeration with Pulp: A Concept to Improve the Economics of Heap leaching", Randol Gold Forum, pp. 150–152 (Sacramento, CA, 1989).

D. Morin and P. Ollivier, "Pilot practice of continuous bioleaching of a refractory gold sulfide concentrate with a high as content", Biohydrometallurgy, pp. 563–576 (1989).

H. Nicholson et al., "Selection of a Refractory Gold Treatment Process for the Sansu Project", pp. 20–1 to 20.11, Ashanti Goldfields Corporation (Ghana) Limited (no year indicated).

A. Nishiwaki et al., "Effect of longitudinal mixing on microbial growth in a multi–stage column reactor," J. Chem. Tech. Biotechnol., vol. 48, pp. 227–237 (1989).

Paul A.R. Odd et al., "Bioleaching—A Feasible Process for Wiluna Refractory Gold Ores", BioMIne'93, 1993 (Adelaide, South Australia), Australian Mineral Foundation.

P. Ollivier and D. Morin, "Bioleaching of Sulfide Concentrates and Ores: Study of Refractory Gold and Non–Ferrous Base Metals Ores", pp. 93–99, Randol Gold Forum (1990) (Olympic Valley, California), Randol International.

G. Pantelis et al., "Optimising Oxidation Rates in Heaps in Pyritic Material", Biohydrometallurgical Technologies, The Minerals, Metals & Materials Society, pp. 731–738 (1993).

G. M. Potter, "Designs Factors for Heap Leaching Operations", Mining Engineering, pp. 277–281 (1981).

J. Parthen et al., "Determination of Technical Parameters for Microbial Soil Cleaning in Bioreactors", DECHEMA Biotechnology Conferences, vol. 4, Part A, pp. 563–567 (1990).

Tommy J. Phelps et al., "Biodegradation of Mixed–Organic Wastes by Microbial Consortia in Continuous–Recycle Expanded–Bed Bioreactors", Envir. Sci. Technol., vol. 25, No. 8, pp. 1461–1465 (1991).

A. Pinches et al., "The Performance of Bacterial Leach Reactors for the Pre–oxidation of Refractory Gold–Bearing Sulphide Concentrates", Biohydrometallurgy, pp. 329–344 (Warwick United Kingdom, Antony Rowe Ltd.) (1987).

Hee W. Ryu et al., "Microbial coal desulfurization in an airlift bioreactor by sulfur–oxidizing bacterium *Thiobacillus ferrooxidans*", Fuel Processing Technology, vol. 36, pp. 267–275 (1993).

S. Sandhya et al., "Kinetics of $Fe^{2+}$ Oxidation in Down Flow Packed Bed Fixed Film Reactors", J. Environ. Sci. Health, A27(2); pp. 445–461 (1992).

T. V. Subrahmanyam et al., "Recovery Problems in Gold Ore Processing with Emphasis on Heap Leaching", Mineral Processing and Extractive Metallurgy Review, vol. 4, pp. 201–215 (1989).

Troy, M. A. et al., "Biological Land Treatment of Diesel Fuel–Contaminated Soil: Emergency Response Through Closure," Bioremediation: Field Experience, pp. 145–160 (Boca Raton, Lewis) (1994).

Oren F. Webb et al., "Development of a Packed Bed Reactor System for Measurement of Xenobiotic Degradation by Microbial Cultures and of Soil Properties" (Abstract), 207th ACS National Meeting (American Chemical Society, San Diego, CA.) (1994).

Xin–Hui Xing et al., "A model analysis of microbial retainment process in porous support particles in a fluidizedbed wastewater treatment reactor," J. Chem. Eng. Japan, vol. 25, No. 1, pp. 89–95 (1992).

J. C. Duarte et al., "Semi–Conductor Reactor Studies of a High Temperature Copper Bioleaching Process", Proceedings of the 6th European Congress on Biotechnology (1994), pp. 1177–1180.

C. Ongcharit et al., "Novel Immobilized Cell Reactor for Microbial Oxidation of $H_2S$", Chemical Engineering Science, vol. 45, No. 8, pp. 2383–2389 (1990).

Harries, J.R. et al., "Rate controls on leaching in pyritic mine wastes", BioHydroMetallurgy (1987) (Warwick United Kingdom), Science and Technology Letters, pp. 233–241.

Silver et al., "Oxidation of metal sulfides by Thiobacillus ferrooxidans grown on different substrates", Can J. Microbiol (1974), 20: pp. 141–147.

Tuovinen, O. et al., "Studies on the growth of Thiobacillus ferrooxidans", II. Toxicity of Uranimum to growing cultures and tolerance conferred by mutation, other metal cations and EDTA, Arch. Microbiol. (1974), pp. 153–164.

Official Notification dated Jul. 30, 1999 from the Hungarian Patent Office for Hungarian National Phase Patent Application No. P9900904 (without translation) and attached Novelty Search Report dated May 19, 1999 from the Hungarian Patent Office for Hungarian National Phase Patent Application No. P9900904 (and translation thereof).

NONSTIRRED BIOREACTOR FOR PROCESSING REFRACTORY SULFIDE CONCENTRATES AND METHOD FOR OPERATING SAME

This application is a continuation of application Ser. No. 08/459,621, filed on Jun. 2, 1995, now abandoned, which is a CIP of Ser. No. 08/343,888, Nov. 16, 1994, now U.S. Pat. No. 5,573,575.

BACKGROUND OF THE INVENTION

1. Field of the Invention

The present invention relates to the recovery of metal values from ores containing sulfide minerals.

2. Description of the Prior Art

Gold is one of the rarest metals on earth. Gold ores can be categorized into two types: free milling and refractory. Free milling ores are those that can be processed by simple gravity techniques or direct cyanidation. Refractory ores, on the other hand, are not amenable to conventional cyanidation treatment. Gold bearing deposits are deemed refractory if they cannot be economically processed using conventional cyanide leaching techniques because insufficient gold is solubilized. Such ores are often refractory because of their excessive content of metallic sulfides (e.g., pyrite and arsenopyrite) and/or organic carbonaceous matter.

A large number of refractory ores consist of ores with a precious metal such as gold occluded in iron sulfide particles. The iron sulfide particles consist principally of pyrite and arsenopyrite. If the gold, or other precious metal, remains occluded within the sulfide host, even after grinding, then the sulfides must be oxidized to liberate the encapsulated precious metal values and make them amenable to a leaching agent (or lixiviant); thus, the sulfide oxidation process reduces the refractory nature of the ore.

A number of processes for oxidizing the sulfide minerals to liberate the precious metal values are well known in the art. These methods can generally be broken down into two types: mill operations and heap operations. Mill operations are typically expensive processes having high operating and capital costs. As a result, even though the overall recovery rate is typically higher for mill type processes, mill operations are typically not applicable to low grade ores, that is ores having a gold concentration less than approximately 0.07 oz/ton. Mill operations are even less applicable to ores having a gold concentration as low as 0.02 oz/ton.

Two well known methods of oxidizing sulfides in mill type operations are pressure oxidation in an autoclave and roasting.

Oxidation of sulfides in refractory sulfide ores can also be accomplished using acidophilic, autotrophic microorganisms, such as *Thiobacillus ferrooxidans, Sulfolobus, Acidianus* species and facultative-thermophilic bacteria in a microbial pretreatment. These microorganisms can utilize the oxidation of sulfide minerals as an energy source during metabolism. During the oxidation process, the foregoing microorganisms oxidize the iron sulfide particles to cause the solubilization of iron as ferric iron, and sulfide, as sulfate ion.

Oxidation of refractory sulfide ores using microorganisms, or as often referred to biooxidation, can be accomplished in a mill process or a heap process. Compared to pressure oxidation and roasting, biooxidation processes are simpler to operate, require less capital, and have lower operating costs. Indeed, biooxidation is often chosen as the process for oxidizing sulfide minerals in refractory sulfide ores because it is economically favored over other means to oxidize the ore. However, because of the slower oxidation rates associated with microorganisms when compared to chemical and mechanical means to oxidize sulfide refractory ores, biooxidation is often the limiting step in the mining process.

One mill type biooxidation process involves comminution of the ore followed by treating a slurry of the ore in a stirred bioreactor where microorganisms can use the finely ground sulfides as an energy source. Such a mill process was used on a commercial scale at the Tonkin Springs mine. However, the mining industry has generally considered the Tonkin Springs biooxidation operation a failure. A second mill type biooxidation process involves separating the precious metal bearing sulfides from the ore using conventional sulfide concentrating technologies, such as floatation, and then oxidizing the sulfides in a stirred bioreactor to alleviate their refractory nature. Commercial operations of this type are in use in Africa, South America and Australia.

Biooxidation in a heap process typically entails forming a heap with crushed refractory sulfide ore particles and then inoculating the heap with a microorganism capable of biooxidizing the sulfide minerals in the ore. After biooxidation has come to a desired end point, the heap is drained and washed out by repeated flushing. The liberated precious metal values are then ready to be leached with a suitable lixiviant.

Typically precious metal containing ores are leached with cyanide because it is the most efficient leachant or lixiviant for the recovery of the precious metal values from the ore. However, if cyanide is used as the lixiviant, the heap must first be neutralized.

Because biooxidation occurs at a low, acidic pH while cyanide processing must occur at a high, basic pH, heap biooxidation followed by conventional cyanide processing is inherently a two step process. As a result, processing options utilizing heap biooxidation must separate the two steps of the process. This is conventionally done by separating the steps temporally. For example, in a heap biooxidation process of a refractory sulfide gold ore, the heap is first biooxidized and then rinsed, neutralized and treated with cyanide. To accomplish this economically and practically, most heap biooxidation operations use a permanent heap pad in one of several ore on—ore off configurations.

Of the various biooxidation processes available, heap biooxidation has the lowest operating and capital costs. This makes heap biooxidation processes particularly applicable to low grade or waste type ores, that is ores having a gold (or an equivalent precious metal value) concentration of less than about 0.07 oz/ton. Heap biooxidation, however, has very slow kinetics compared to mill biooxidation processes. Heap biooxidation can require many months in order to sufficiently oxidize the sulfide minerals in the ore to permit the gold or other precious metal values to be recovered in sufficient quantities by subsequent cyanide leaching for the process to be considered economical. Heap biooxidation operations, therefore, become limited by the length of time required for sufficient biooxidation to occur to permit the economical recovery of gold. The longer the time required for biooxidation the larger the permanent pad facilities and the larger the necessary capital investment. At mine sites where the amount of land suitable for heap pad construction is limited, the size of the permanent pad can become a limiting factor in the amount of ore processed at the mine and thus the profitability of the mine. In such circumstances, rate limiting conditions of the biooxidation process become even more important.

The rate limiting conditions of the heap biooxidation process include inoculant access, nutrient access, air or oxygen access, and carbon dioxide access, which are required to make the process more efficient and thus an attractive treatment option. Moreover, for biooxidation, the induction times concerning biooxidants, the growth cycles, the biocide activities, viability of the bacteria and the like are important considerations because the variables such as accessibility, particle size, settling, compaction and the like are economically irreversible once a heap has been constructed. As a result, heaps cannot be repaired once formed, except on a limited basis.

The methods disclosed in U.S. Pat. No. 5,246,486, issued Sep. 21, 1993, and U.S. Pat. No. 5,431,717, issued Jul. 11, 1995 to William Kohr, both of which are hereby incorporated by reference, are directed to increasing the efficiency of the heap biooxidation process by ensuring good fluid flow (both gas and liquid) throughout the heap.

Solution inventory and solution management, however, also pose important rate limiting considerations for heap biooxidation processes. The solution drained from the biooxidation heap will be acidic and contain bacteria and ferric ions. Therefore, this solution can be used advantageously in the agglomeration of new ore or by recycling it back to the top of the heap. However, toxic and inhibitory materials can build up in this off solution. For example, ferric ions, which are generally a useful aid in pyrite leaching, are inhibitory to bacteria growth when their concentration exceeds about 30 g/L. Other metals that retard the biooxidation process can also build-up in this solution. Such metals that are often found in refractory sulfide ores include arsenic, antimony, cadmium, lead, mercury, and molybdenum. Other toxic metals, biooxidation byproducts, dissolved salts and bacterially produced material can also be inhibitory to the biooxidation rate. When these inhibitory materials build up in the off solution to a sufficient level, recycling of the off solution becomes detrimental the rate at which the biooxidation process proceeds. Indeed, continued recycling of an off solution having a sufficient build-up of inhibitory materials will stop the biooxidation process altogether.

The method disclosed in U.S. patent application Ser. No. 08/329,002, filed Oct. 25, 1994, by Kohr, et al., hereby incorporated by reference, teaches a method of treating the bioleachate off solution to minimize the build-up of inhibitory materials. As a result, when the bioleachate off solution is recycled to the top of the heap, the biooxidation rate within the heap is not slowed, or it will be slowed to a lesser degree than if the off solution were recycled without treatment.

While the above methods have improved the rate at which heap biooxidation processes proceed, heap biooxidation still takes much longer than a mill biooxidation process such as a stirred bioreactor. Yet, as pointed out above, with low grade refractory sulfide ores, a stirred bioreactor is not a viable alternative due to its high initial capital cost and high operating costs.

In addition to refractory sulfide precious metal ores, there are many other ores which contain metal sulfide minerals which could potentially be treated using a biooxidation process. For example, many copper ores contain copper sulfide minerals. Biooxidation could be used to process concentrates of these ores to liberate the copper or other metal which could then be recovered by known solvent extraction techniques. However, due to the sheer volume of the sulfide concentrate in these ores, a stirred bioreactor would be prohibitively expensive, and standard heap operations would simply take too long to make it economically feasible to recover the desired metal values.

Therefore, while a need exists for a method of biooxidation that can be used to process sulfide concentrates from refractory sulfide ores at a rate which is much faster than that of existing heap biooxidation processes, yet which has initial capital costs and operating costs less than that of a stirred bioreactor, this need has gone unfulfilled. Further, while a need has also existed for a method of biooxidation that can be used to economically process sulfide concentrates of metal sulfide type ores, this need has also gone unfulfilled.

SUMMARY OF INVENTION

It is an object of the present invention to provide a method of biooxidation that satisfies the above described needs. To this end, a method of biooxidizing sulfide minerals in a nonstirred bioreactor is provided. The method comprises coating a concentrate of sulfide minerals onto a plurality of coarse substrates, such as coarse ore particles, lava rock, gravel, or rock containing small amounts of mineral carbonate as a source of $CO_2$ for the bacteria. After the sulfide minerals are coated or spread onto the plurality of substrates, a heap is formed with the coated substrates or the coated substrates particles are placed within a tank. The sulfide minerals on the surface of the plurality of coated substrates are then biooxidized to liberate the metal value of interest.

Depending on the particular ore deposit being mined, the sulfide mineral concentrates used in this invention may comprise sulfide concentrates from precious metal bearing refractory sulfide ores or they may comprise sulfide concentrates from base metal sulfide type ores, such as chalcopyrite, pyrite or sphalorite. The distinction being that in the former, the metal of interest is a precious metal occluded within the sulfide minerals, and in the latter, the metal to be recovered is a base metal such as copper, iron, or zinc and is present as a metal sulfide in the sulfide concentrate.

The above and other objects, features, and advantages will become apparent to those skilled in the art from the following detailed description of the invention.

DETAILED DESCRIPTION OF THE INVENTION

Figure 1:
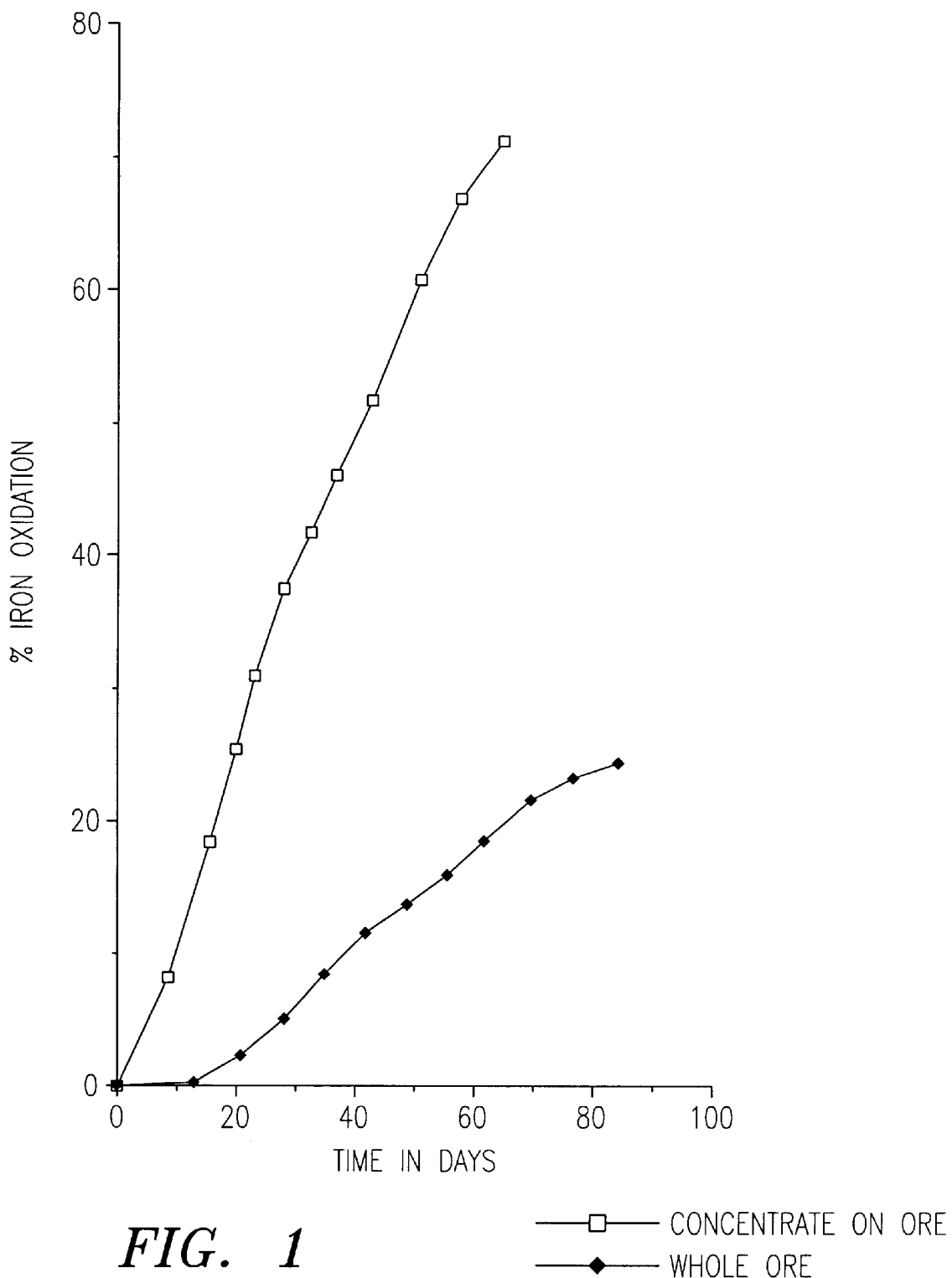
FIG. 1 is a graph illustrating the percent of iron oxidation versus time for a whole ore compared to a process according to the present invention.

The process according to the present invention is now described by way of example. As those skilled in the art will appreciate, however, the process according to the present invention is not limited to the preferred embodiments described herein.

EXAMPLE 1

A sample of low grade (3.4 ppm) gold ore, which was known to be refractory to leaching with cyanide due to sulfides, was crushed. The ore was then separated into a -¼ inch fraction (47.4 wt %) and a -⅛ inch fraction (remainder). The -⅛ inch fraction was then further ground to 95% passing a 200 mesh sieve to aid in producing a refractory pyrite concentrate by flotation.

Water was added to the ground sample until it reached a 30% pulp density. The ore pulp was then adjusted to a pH of 10 and treated with $Na_2SiO_3$ at 6 Kg/tonne of ore for 12 hours to remove the clay material. The clay material was removed as the fraction that did not settle after 12 hours.

Because clays can cause problems with flotation, a step that permits the non clay material to settle out was added to remove the clay fraction before floating the sample.

The clay fraction was under 3% of the total ore weight, yet it contained almost 5% of the gold in the ore. The removal and subsequent flotation of the clay fraction produced a very small weight fraction (0.1% of the total ore weight), but it contained over 17 ppm gold. Cyanide leaching of the clay flotation tail extracted over 76% of the gold contained therein. The total amount of gold contained in the clay flotation tail was 8 ppm.

Before floating, the main fraction of ground ore (+5 mm to -200 mesh) was conditioned with $CaSO_4$ at 2.0 Kg/tonne for ten minutes by mixing in a Wemco flotation cell. This was followed by 10 minutes of mixing with Xanthate at 100 g/tonne which was then followed by 5 minutes of mixing with Dowforth D-200 at 50 g/tonne. The sample was then floated for 20 minutes at a pulp density of 30%. Four Kg of the main fraction was processed in 8 separate batches of 500 g each. The sulfide concentrates obtained from these flotations were collected and combined and refloated in a column.

Three fractions were collected, the tail from the Wemco float, the tail from the column float, and the sulfide concentrate, each of these fractions were dried and weighed. The tail from the Wemco float was 35.4 wt % of total ore weight and contained 1.88 ppm of gold. Cyanide leaching of this fraction yielded 67% of its gold. This was higher than the recovery for cyanide leaching of the whole ore, which was 63%. The column tail contained 3.56 ppm of told. The told recovery from this fraction by cyanide leaching was 76.6%.

The sulfide concentrate weighed 753 g which represented 8.8% of the total ore (+⅛ and -⅛ inch fractions). Analysis of a small fraction of the concentrate indicated it contained 6.5 ppm of gold. This fraction was coated on to the 47.4 weight percent of the +⅛ inch ore. The dry pyrite concentrate was spread over the surface of the coarse ore by rolling in a drum rotating at 30 rpm while spraying a mixture of 2,000 ppm ferric ion and 1% Nalco #7534, which is an agglomeration aid. The pH of the solution was 1.8.

The mixture of concentrate on coarse ore support was placed into a 3 inch column. Air and liquid were introduced from the top. The column was inoculated with 10 ml of bacteria at an O.D. of 2.6 or about $1.1 \times 10^{10}$ bacteria per ml.

The bacteria were grown in an acidic nutrient solution containing 5 g/l ammonium sulfate and 0.83 g/l magnesium sulfate heptahydrate. The pH of the solution was maintained in the range of 1.7 to 1.9 by adjustment with sulfuric acid ($H_2SO_4$). The solution also contained iron at 20 g/liter in the form of ferric and ferrous sulfate.

The bacteria were added to the top of the column after the pH was adjusted to a pH of 1.8. The liquid, introduced to the top of the column throughout the experiment, was pH 1.8; with 0.2×9 K salts and 2,000 ppm ferric. The extent of iron oxidation was determined by analysis of the solution eluting off the column minus the iron introduced by the 2,000 ppm ferric feed.

The composition of the standard 9 K salts medium for *T. ferrooxidans* is listed below. The concentrations are provided in grams/liter.

| | |
|---|---|
| $(NH_4)SO_4$ | 5 |
| KCl | 0.17 |
| $K_2HPO_4$ | 0.083 |
| $MgSO_4.7H_2O$ | 0.833 |
| $Ca(NO_3).4H_2O$ | 0.024 |

The notation 0.2×9 K salts indicates that the 9 K salt solution strength was at twenty percent that of the standard 9 K salt medium.

After 60 days the amount of iron leached off of the column indicated that about 50% of the pyrite had been biooxidized. The experiment was stopped and the mixture separated into a +30 mesh fraction and a -30 mesh fraction. Each fraction was ground to 95% minus 200 mesh and then leached with a 500 ppm cyanide solution in a 96 hour bottle roll analysis. Activated carbon was added to the bottle roll test to absorb any dissolved gold.

The gold recovery of the —30 mesh fraction was 83.7%. The -30 mesh material had an increased head gold value of 8.87 ppm due to loss of pyrite weight. The coarse +30 mesh fraction, on the other hand, had a gold recovery of 57 and a head gold value of 2.24 ppm. This indicated that the pyrite concentrate that was coated on the outside of the coarse rock had biooxidized faster than the coarse fraction of the rock.

EXAMPLE 2

Another comparative test was made. In this example, the biooxidation rates of ore size fractions were compared. The ore, which was provided by the Ramrod Gold Corporation, was crushed to -¾ inch. The -⅛ inch ore fraction was removed and used to form a concentrate. The ore sample had less than 0.08 oz. of gold per ton of ore (2.7 ppm). The sample contained both arsenopyrite and pyrite. The concentrate was made by ball milling 5 Kg of the -⅛ inch ore until it passed -200 mesh, the ball milled ore was then floated with Xanthate to form a pyrite concentrate. Before flotation clay was removed by settling with $Na_2SiO_3$ at 6 Kg/tonne of ore for 8 hours or more. The flotation was done in small batches of 500 g each in a laboratory Wemco flotation cell. Potassium Amyl Xanthate was used as a collector at a concentration of 100 g/tonne along with sodium sulfide at 1.5 Kg/tonne and Dowfroth D-200 at 50 g/tonne. The pyrite concentrate constituted 4.5% of the weight of the -⅛ inch ore fraction. However, this ore fraction contained over 80% of the gold and pyrite for the milled ore. The concentrate contained approximately 17.4% iron, 15.7% sulfur and approximately 40 ppm gold. The +⅛ inch ore contained 0.9% iron and 0.18% sulfur.

A sample of 140 g of this concentrate was coated onto 560 g of +⅛ inch coarse ore. The concentrate was added as a dry powder to the coarse ore. The mixture was then rotated in a small plastic drum at 30 rpm to spread the dry concentrate over the rock support. Liquid which contained 2,000 ppm ferric ion and 1% Nalco #7534 was sprayed onto the mixture until all the concentrate was coated onto the rock. The pH of the liquid was maintained at 1.8. The amount of liquid used was estimated to be between 5 and 10 percent of the weight of the rock and concentrate. The 700 g mixture of concentrate on substrates was placed into a 3 inch column. The height of the ore after being placed in the column was approximately 5 inches. Air and liquid were introduced from the top of the column. The column of concentrate coated coarse ore substrates was inoculated with about 10 ml of bacteria at an O.D. of 2.0 or about $8 \times 10^9$ bacteria per ml.

The bacteria were a mixed culture of Thiobacillus, which were originally started with ATCC strains #19859 and 33020. The bacteria were grown in an acidic nutrient solution containing 5 g/l ammonium sulfate and 0.83 g/l magnesium sulfate heptahydrate. The pH of the solution was maintained in the range of 1.7 to 1.9 by adjustment with sulfuric acid ($H_2SO_4$). The solution also contained iron at 20 g/liter in the form of ferric and ferrous sulfate.

The bacteria were added to the top of the column after the pH was adjusted to pH 1.8. The liquid, introduced to the top of the column throughout the experiment had a pH of 1.8 with 0.2×9 K salts and 2,000 ppm ferric ion. The extent of iron oxidation was determined by analysis of the solution eluting off the column minus the iron introduced by the 2,000 ppm ferric feed.

Figure 2:
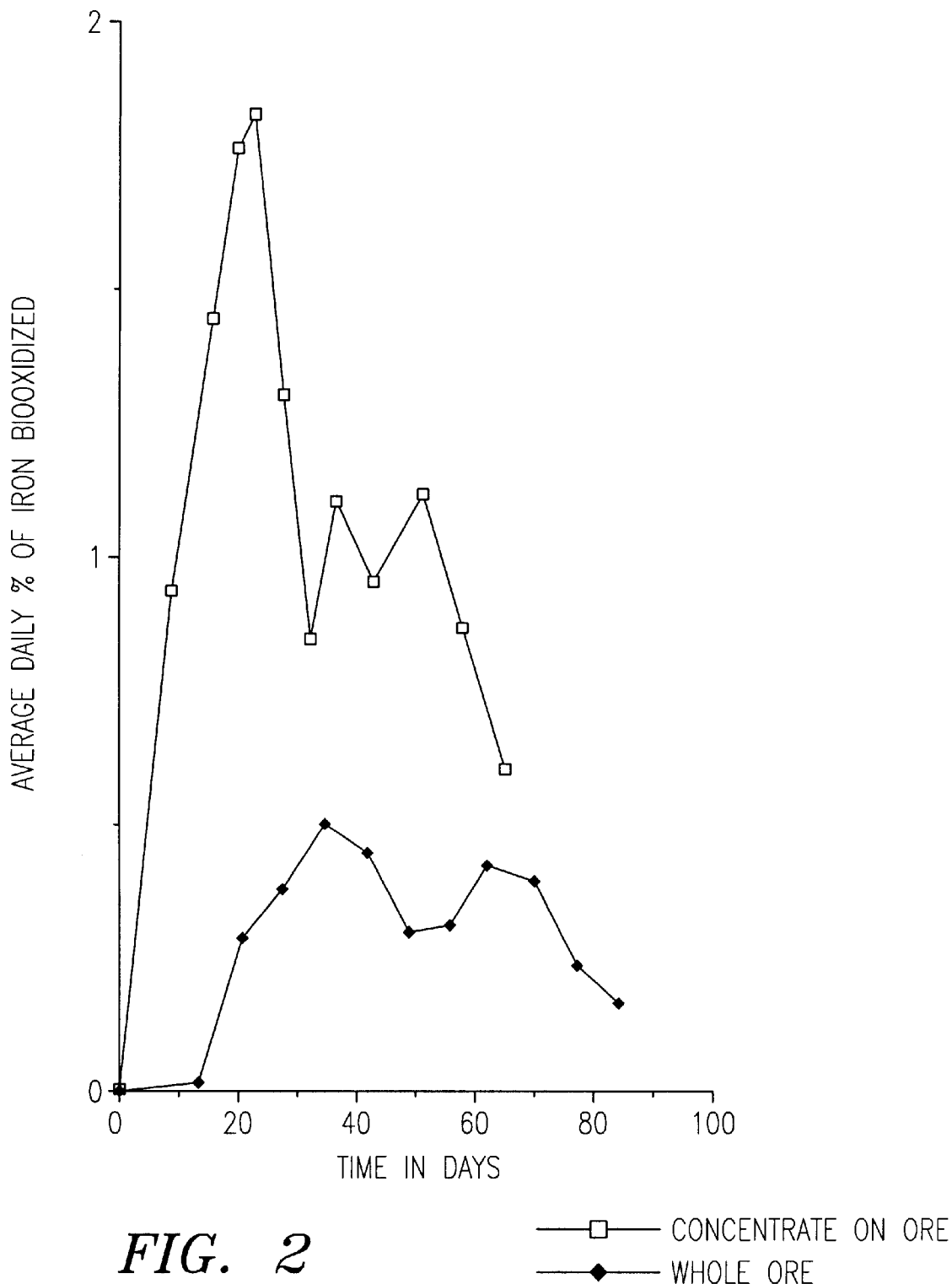
FIG. 2 is a graph comparing the average daily biooxidation rate of a whole ore against that of a process according to the present invention.

This ore was low in sulfides having a concentration of less than 1% of its weight. By making a concentrate on the coarse rock at 20% by weight, the concentration of both the pyrite and gold could be increased by over tenfold. This increased the rate of biooxidation, as seen in FIGS. 1 and 2, over that for the whole ore. Not only did this process expose more of the pyrite to air and water but it also increased the amount of ferric ion and acid generated per unit volume of ore in the column model for a heap.

FIG. 1 shows the amount of oxidation as determined by percent iron leached for both the pyrite concentrate of this ore on +⅛ inch coarse ore and the whole ore itself. As the graph shows the concentrate process was biooxidized to about 40% in the first 30 days and over 65% in the first 60 days. Whereas the whole ore was only biooxidized to 24% in 84 days. The average daily biooxidation rates are shown in FIG. 2. The highest average daily rate of the coated concentrate was 1.8% per day compared to an average daily rate of only 0.5% for the whole ore. As FIG. 2 illustrates, the coated concentrate on coarse ore sample did not take as long to begin biooxidizing as the whole ore sample. This means that the coated concentrate process is more likely to achieve complete biooxidation in a reasonably short time.

Table 1 below shows the specific data points graphed in FIGS. 1 and 2 for the concentrate on coarse ore process and for the whole ore process which was done for comparison.

After 68 days the coated concentrate on coarse ore column was taken down. The biooxidized material was separated into a plus 80 mesh fraction and a minus 80 mesh fraction. The weight of the fine material had increased from 140 g to 150 g. The total amount of iron removed from the system during the 68 days of biooxidation was 21.5 g which represents 46 g of pyrite. The weight of the coarse rock decreased by 54 g. This was believed to be due to breakdown of the rock to finer material due to the biooxidation process. The total weight after biooxidation was 656 g which was 44 g, less than the starting material. This fit well with the estimated 46 g of pyrite oxidized.

TABLE 1

| Concentrate Process | | | Whole Ore Process | | |
|---|---|---|---|---|---|
| # of Days | % Fe leached | % Fe/day | # of days | % Fe Leached | % Fe/day |
| 0 | 0.0 | 0.00 | 0 | 0.0 | 0.00 |
| 9 | 8.4 | 0.93 | 13 | 0.2 | 0.01 |

TABLE 1-continued

| Concentrate Process | | | Whole Ore Process | | |
|---|---|---|---|---|---|
| # of Days | % Fe leached | % Fe/day | # of days | % Fe Leached | % Fe/day |
| 16 | 18.5 | 1.44 | 21 | 2.5 | 0.29 |
| 20 | 25.5 | 1.76 | 28 | 5.1 | 0.38 |
| 23 | 31.0 | 1.82 | 35 | 8.6 | 0.50 |
| 28 | 37.5 | 1.30 | 42 | 11.7 | 0.44 |
| 33 | 41.7 | 0.84 | 49 | 13.8 | 0.29 |
| 37 | 46.1 | 1.10 | 56 | 15.9 | 0.31 |
| 43 | 51.8 | 0.95 | 62 | 18.4 | 0.42 |
| 51 | 60.7 | 1.11 | 70 | 21.5 | 0.39 |
| 58 | 66.7 | 0.86 | 77 | 23.1 | 0.23 |
| 65 | 70.9 | 0.60 | 84 | 24.3 | 0.16 |

Two samples of the −80 mesh material and one sample of the +80 mesh material were leached with cyanide. To leach the samples, bottle rolls were done for 96 hours, the leachant was maintained at 500 ppm cyanide. The +80 mesh coarse ore support rock was ground to 95% −200 mesh before doing the bottle roll. All bottle rolls were done with activated carbon in the leach solution.

Sulfide analysis of the minus 80 mesh fraction after 68 days of biooxidation showed the sample still contained 8.8% sulfides which was 56% of the starting level. This was a lower percent oxidation than indicated by the iron leached off during the column experiment. The gold recovery increased to 84.3% for the high grade (38 ppm) −80 mesh fraction and 79.5% for the +80 mesh low grade (3 ppm) fraction. This is a substantial increase from the 45.6% recovery of the unoxidized ore.

EXAMPLE 3

A sample of 70% minus 200 mesh gold ore from a mine in the Dominican Republic was used to make a sulfide float concentrate. The ore sample was obtained from the tailing pile at the mine that had already been leached with cyanide. The ore sample still contained gold values of over 2 g per tonne which were occluded within the sulfides and not directly leachable by cyanide.

Several kilograms of this sample were further ground to 95% minus 200 mesh. The ground sample was then floated to form a sulfide concentrate. The flotation was done in small batches of 500 g each in a laboratory Wemco flotation cell. Before flotation, the ground ore sample was adjusted to a pulp density of 30% The ore slurry was then mixed with 1.5 Kg/tonne sodium sulfide ($Na_2S$) for 5 minutes at pH 8.5. Then potassium amyl Xanthate was added as a collector at 100 g/tonne and mixed for 5 minutes. Next 50 g/tonne of Dowfroth D-200 was added and mixed for 5 minutes. Finally, air was introduced to produce a sulfide concentrate that contained 17.4% iron and 19.4% sulfide by weight and 14 g of gold per tonne of concentrate. A plurality of concentrate coated coarse substrates were then made by coating of 140 g of sulfide concentrate onto 560 g of +⅛ inch −¼ inch granite rock. The concentrate was added as a dry powder to the granite rock. The mixture was then rotated in a small plastic drum at 30 rpm to spread the dry pyrite over the support material. A liquid which contained 2,000 ppm ferric sulfide and 1% Nalco #7534 agglomeration aid was sprayed on the mixture until all the sulfide concentrate was coated onto the wetted granite rock. The solution was maintained at a ph of 1.8.

The coarse rock in this case had no iron or gold value. The rock, however, contained a small amount of mineral carbonate which tended to keep the pH high at first but also provided $CO_2$ as a carbon source for the bacteria.

The 700 g of concentrate coated rock was put into a column. A 0.2×9 K salts and 2,000 ppm ferric iron solution having a ph of 1.6 was introduced through the top of the column at a flow rate of about 300 ml/day. Then the column was inoculated with 10 ml of bacteria as in Example 2. After the pH of the concentrate coated rock substrate was adjusted to a pH of 1.8 the pH of the influent was set at 1.8. Air was also introduced through the top of the column.

Figure 3:
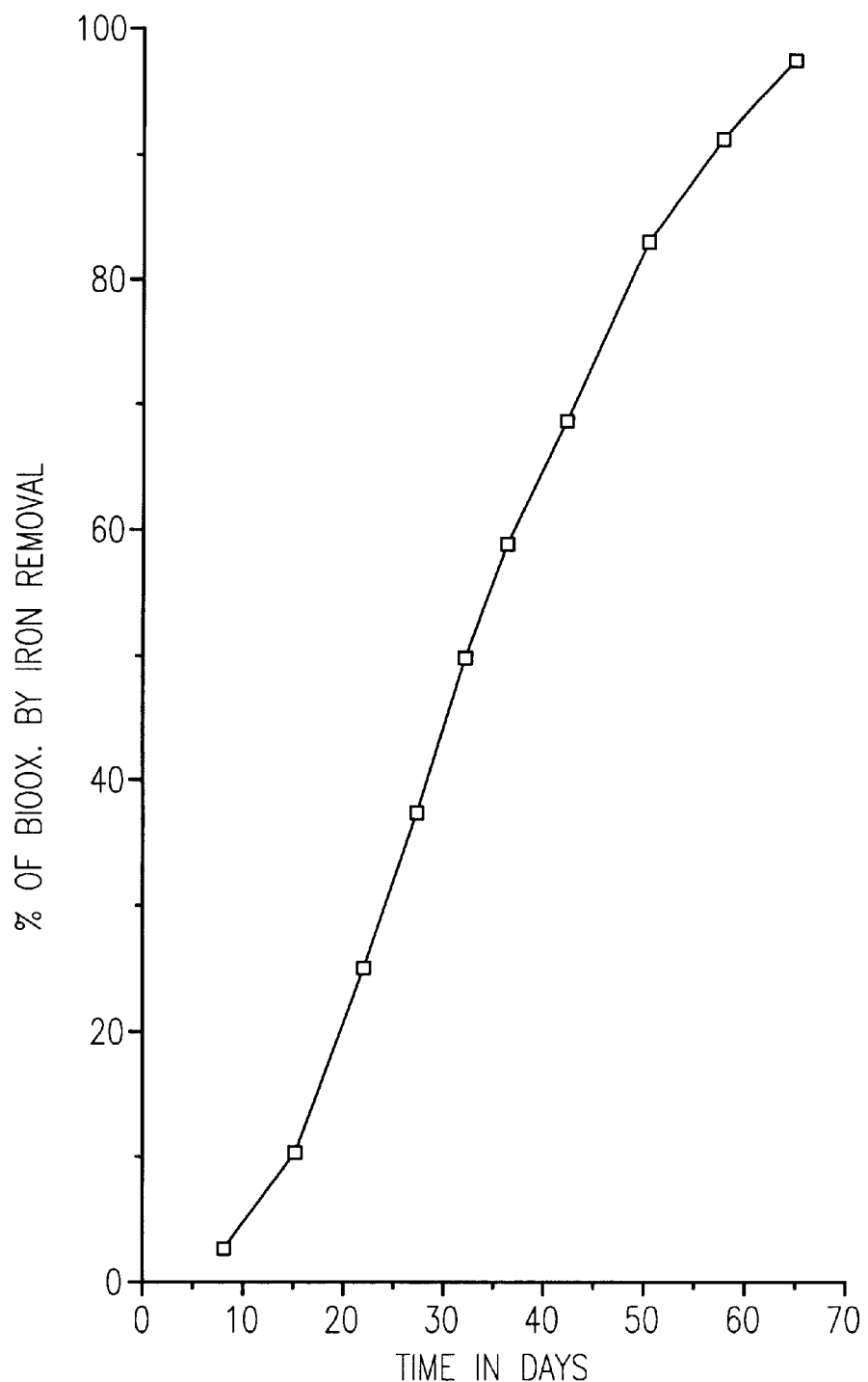
FIG. 3 is a graph illustrating the percentage of biooxidation for another process according to the present invention.
Figure 4:
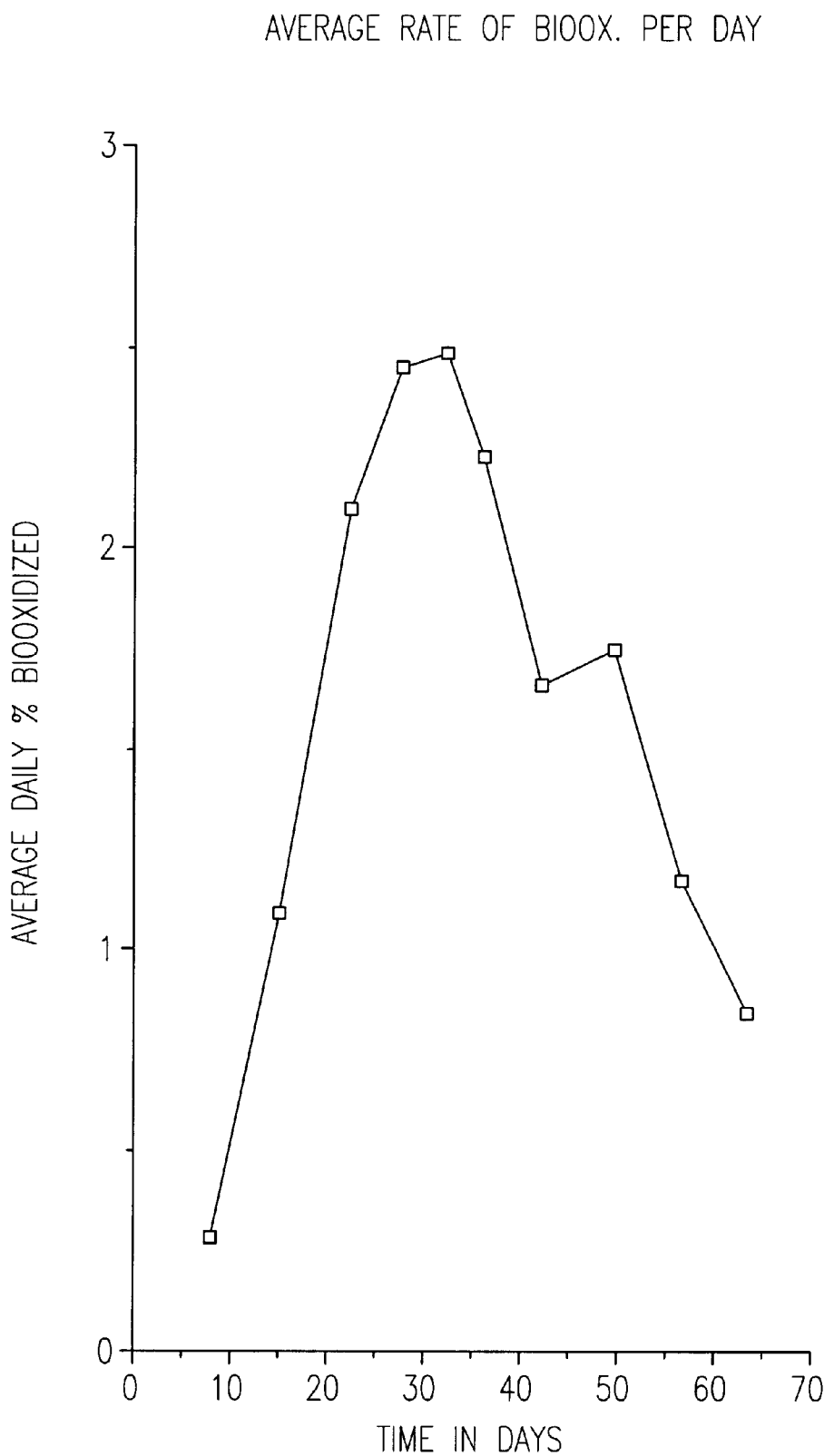
FIG. 4 is a graph illustrating the average daily rate of biooxidation for the process corresponding to FIG. 4.

FIG. 3 graphically illustrates the percent of biooxidation as determined by the percent of iron leached from the concentrate. The average daily percentage of biooxidation was calculated and is listed in Table 2 and is graphically illustrated in FIG. 4. The percentage biooxidation was determined by dividing the total iron removed by the total iron contained within the concentrate. The rate of biooxidation was slow to start as the pH was adjusted and the bacteria built up and adapted. However, after about two weeks the rate increased rapidly and reached a maximum after 30 days. By this time almost 50% of the total iron had been biooxidized. The process continued with a gradual slowdown as the remaining pyrite was consumed. At the end of 64 days nearly 97% of the iron had been biooxidized. Even with the concentrate almost completely biooxidized and the rate slowing down near the end of the process, the average daily rate was still near 1%/day. After 70 days the biooxidation was stopped. The biooxidized concentrate was separated into a plus 80 mesh fraction and a minus 80 mesh fraction. The weight of the biooxidized concentrate had decreased from 140 g to 115 g. The total amount of iron removed from the system during the 70 days of biooxidation was 25.9 g which represents 55.5 g of pyrite. The weight of the granite rock decreased by 98.8 g. This was believed to be due to a breakdown of the calcium carbonate in the rock by the acid as well as the breakdown of the rock to finer material. The total weight decreased by 123.3 g which was 67.8 g more than predicted by biooxidation of pyrite alone.

TABLE 2

| Time in Days | % Bioox. | % Bioox./Day |
| --- | --- | --- |
| 5 | 2.590 | 0.288 |
| 15 | 10.270 | 1.100 |
| 22 | 24.970 | 2.100 |
| 27 | 37.250 | 2.450 |
| 32 | 49.700 | 2.490 |
| 36 | 58.610 | 2.230 |
| 42 | 68.580 | 1.660 |
| 50 | 82.580 | 1.750 |
| 57 | 90.870 | 1.180 |
| 64 | 96.820 | 0.850 |

The sample of −80 mesh material was leached with 500 ppm cyanide in a bottle roll for 96 hours. The +80 mesh granite rock was also leached with 500 ppm cyanide to determine how much gold could be stuck to the support rock in a process that used barren rock as a supporting substrate. Analysis of the −80 mesh material showed it still contained 9.7% sulfide which indicated only about 50% oxidation.

Gold extraction was 77% of the −80 mesh fraction. This gold was recovered from gold ore that had already been leached with cyanide, thus demonstrating that the process according to the present invention is even applicable to ores which heretofore have been considered waste. And while any recovery would be an improvement over the process currently practiced at the mine, the process according to the present invention was able to recover 77% of the gold in what was previously considered tailings.

Cyanide leaching of the granite support rock showed that it had picked up 0.15 ppm of gold which was 3.4% of the total gold.

Although the invention has been described with reference to preferred embodiments and specific examples, it will readily be appreciated by those of ordinary skill in the art that many modifications and adaptions of the invention are possible without departure from the spirit and scope of the invention as claimed hereinafter. For example, while the processes according to the present invention have been described in terms of recovering gold from refractory sulfide or refractory carbonaceous sulfide ores, the processes are equally applicable to other precious metals found in these ores such as silver and platinum. Similarly, the process according to the present invention may, as one skilled in the art would readily recognize, be used to biooxidize sulfide concentrates from metal sulfide ores such as chalcopyrite and sphalorite.

I claim:

1. A method of increasing the average heap biooxidation rate of a crushed sulfide mineral bearing whole ore comprising the steps of:
   a. forming a concentrate of sulfide minerals from the sulfide mineral bearing ore;
   b. coating a plurality of coarse substrates with the sulfide mineral concentrate;
   c. forming a heap with said plurality of concentrate coated substrates and bacteria capable of biooxidizing sulfide minerals; and
   d. biooxidizing said sulfide mineral concentrate on the surface of said plurality of coarse substrates, the average biooxidation rate being at least two times greater than the average heap biooxidation rate of the crushed sulfide mineral bearing whole ore.

2. A method according to claim 1, wherein the plurality of coarse substrates is a material selected from the group consisting of coarse ore particles, lava rock, gravel, and rock containing mineral carbonate.

3. A method according to claim 1, wherein the amount of said concentrate coated onto said plurality of coarse substrates is approximately 16 to 20% of the combined weight of said concentrate and said coarse substrates.

4. A method according to claim 1, wherein said plurality of coarse substrates comprise coarse ore particles that contain metal sulfide particles.

5. A method according to claim 1, wherein said plurality of coarse substrates comprise barren rock.

6. A method according to claim 5, wherein said barren rock includes a carbonate mineral component.

7. A method according to claim 1, wherein said coarse substrates have a particle size greater than ⅛ inch.

8. A method according to claim 7, wherein said coarse substrates have a particle size of less than ¾ inch.

9. A method according to claim 1, wherein said sulfide mineral concentrate has a particle size of 95% minus 200 mesh.

10. A method according to claim 1, wherein said sulfide mineral concentrate comprises a sulfide mineral concentrate produced from a precious metal bearing refractory sulfide ore.

11. A method according to claim 1, wherein said sulfide mineral concentrate comprises a sulfide mineral concentrate produced from a base metal sulfide ore.

12. A method according to claim 1, wherein said concentrate is coated onto said plurality of coarse substrates by mixing said concentrate and said plurality of coarse substrates in a rotating drum and adding an aqueous solution to the rotating drum until said concentrate is coated onto said plurality of coarse substrates.

13. A method according to claim 12, wherein the amount of aqueous solution added to the rotating drum is between 5 and 10 weight percent of the combined weight of said concentrate and said plurality of coarse substrates.

14. A method of increasing the average biooxidation rate of a sulfide mineral bearing ore comprising the steps of:
   a. forming a concentrate of sulfide minerals from the sulfide mineral bearing ore;
   b. coating a plurality of coarse ore substrates with the sulfide mineral concentrate;
   c. forming a heap with said plurality of coated ore substrates; and
   d. biooxidizing said sulfide mineral concentrate on the surface of the plurality of coarse ore substrates.

15. A method according to claim 14, the average biooxidation rate being at least two times greater than the biooxidation rate of sulfide mineral bearing whole ore.

16. A method according to claim 14, wherein the amount of said concentrate coated onto said plurality of coarse ore substrates is approximately 16 to 20% of the combined weight of said concentrate and said coarse substrates.

17. A method according to claim 14, wherein said coarse ore substrates have a particle size greater than ⅛ inch.

18. A method according to claim 17, wherein said coarse ore substrates have a particle size of less than ¾ inch.

19. A method according to claim 14, wherein said sulfide mineral concentrate has a particle size of 95% minus 200 mesh.

20. A method according to claim 14, wherein said sulfide mineral concentrate comprises a sulfide mineral concentrate produced from a precious metal bearing refractory sulfide ore.

21. A method according to claim 14, wherein said sulfide mineral concentrate comprises a sulfide mineral concentrate produced from a base metal sulfide ore.

22. A method according to claim 14, wherein said concentrate is coated onto said plurality of coarse ore substrates by mixing said concentrate and said plurality of coarse ore substrates in a rotating drum and adding an aqueous solution to the rotating drum until said concentrate is coated onto said substrates of coarse ore particles.

23. A method according to claim 22, wherein the amount of aqueous solution added to the rotating drum is between 5 and 10 weight percent of the combined weight of said concentrate and said substrates of coarse ore particles.

* * * * *

UNITED STATES PATENT AND TRADEMARK OFFICE
CERTIFICATE OF CORRECTION

PATENT NO. : 6,107,065
DATED : August 22, 2000
INVENTOR(S) : William J. Kohr

It is certified that error appears in the above-identified patent and that said Letters Patent is hereby corrected as shown below:

Title page, item [63], delete ", which is a CIP of Ser. No. 08/343,888, Nov. 16, 1994, now U.S. Pat. No. 5,573,575"

Column 1, lines 7-9, delete ", which is a CIP of Ser. No. 08/343,888, Nov. 16, 1994, now U.S. Pat. No. 5,573,575"

Signed and Sealed this

Fifth Day of December, 2000

*Attest:*

Q. TODD DICKINSON

*Attesting Officer*   *Director of Patents and Trademarks*

UNITED STATES PATENT AND TRADEMARK OFFICE
CERTIFICATE OF CORRECTION

PATENT NO. : 6,107,065
DATED : August 22, 2000
INVENTOR(S) : William J. Kohr

It is certified that error appears in the above-identified patent and that said Letters Patent is hereby corrected as shown below:

<u>Title page,</u>
Item [56], following "OTHER PUBLICATIONS", change "D. Morin and P. Ollivier, "Pilot practice of continuous bioleaching of a refractory gold sulfide concentrate with a high as content", Biohydrometallurgy, pp. 563-576 (1989)." to read -- D. Morin and P. Ollivier, "Pilot practice of continuous bioleaching of a refractory gold sulfide concentrate with a high As content", Biohydrometallurgy, pp. 563-576 (1989). --.

<u>Column 3,</u>
Line 40, insert -- to -- between "detrimental" and "the".

<u>Column 4,</u>
Line 4, change "lcong" to read -- long --.
Line 27, delete "particles".

<u>Column 5,</u>
Line 22, change "mm" to read -- µm --.
Lines 39 and 40, change "told" to read -- gold --.

<u>Column 6,</u>
Line 27, change "57" to read -- 57% --.
Line 65, insert -- coarse ore -- between "on" and "substrate".

<u>Column 7,</u>
Line 4, change "Thiobacillus" to read -- <u>Thiobacillus ferrooxidans</u> --.
Line 39, insert -- the -- between "on" and "coarse".
Line 56, change "g, less" to read -- g less --.

<u>Column 8,</u>
Line 48, change "30% The" to read -- 30%. The --.
Line 57, change "coating of 140 g" to read -- coating 140 g --.

<u>Column 9,</u>
Line 5, change "ph" to read -- pH --.
Line 9, change "1.8 the" to read -- 1.8, the --.

UNITED STATES PATENT AND TRADEMARK OFFICE
CERTIFICATE OF CORRECTION

PATENT NO.   : 6,107,065
DATED        : August 22, 2000
INVENTOR(S)  : William J. Kohr It is certified that error appears in the above-identified patent and that said Letters Patent is hereby corrected as shown below:

<u>Column 12,</u>
Lines 20 and 25, change "substrates of coarse ore particles." to read -- plurality of coarse ore substrates. --.

Signed and Sealed this

Twenty-fifth Day of June, 2002

*Attest:*

JAMES E. ROGAN
*Director of the United States Patent and Trademark Office*

*Attesting Officer*